United States Patent [19]

Hilbert et al.

[11] Patent Number: 4,920,118

[45] Date of Patent: Apr. 24, 1990

[54] AROMATIC 2-AMINOALKYL-1,2-BENZOISOTHIAZOL-3-(2H)ONE-1,1-DIOXIDE AND THEIR USE AS ANXIOLYTIC AND ANTI-HYPERTENSIVE AGENTS

[75] Inventors: Marcel Hilbert, Strasbourg; Maurice W. Gittos, Plobsheim, both of France

[73] Assignee: Merrell Dow Pharmaceuticals Inc., Cincinnati, Ohio

[21] Appl. No.: 366,824

[22] Filed: Jun. 15, 1989

Related U.S. Application Data

[62] Division of Ser. No. 244,894, Sep. 12, 1988, Pat. No. 4,857,526, which is a division of Ser. No. 158,432, Feb. 22, 1988, Pat. No. 4,789,676, which is a division of Ser. No. 836,276, Mar. 5, 1986, Pat. No. 4,748,182.

[51] Int. Cl.$^5$ .................. A61K 31/38; C07D 279/12; C07D 295/00
[52] U.S. Cl. ............................ 514/224.2; 544/58.7
[58] Field of Search ................ 544/58.7; 514/224.2

[56] References Cited

U.S. PATENT DOCUMENTS 4,789,675 12/1988 Meguro et al. ................ 544/105

Primary Examiner—Mary C. Lee
Assistant Examiner—J. Richter
Attorney, Agent, or Firm—Michael J. Sayles

[57] ABSTRACT

This invention relates to aromatic 2-aminoalkyl derivatives of 1,2-benzoisothiazol-3(2H)one-1,1-dioxides, processes for the preparation of same, and to their use as anxiolytic and antihypertensive agents.

13 Claims, No Drawings

AROMATIC 2-AMINOALKYL-1,2-BENZOISOTHIAZOL-3-(2H)ONE-1,1-DIOXIDE AND THEIR USE AS ANXIOLYTIC AND ANTI-HYPERTENSIVE AGENTS

FIELD OF THE INVENTION

This invention relates to certain aromatic 2-aminoalkyl-1,2-benzoisothiazol-3(2H)one-1,1-dioxide derivatives and their use as anxiolytic agents and antihypertensive agents.

BACKGROUND OF THE INVENTION

Anxiety has been defined as an apprehension or concern regarding some future event. Most, if not all, people occasionally suffer some symptoms of anxiety in response to appropriate stimuli. In some individuals, these feelings of anxiety or panic in response to the everyday pressures of life can be overwhelming, rendering the individual an unproductive member of society. Whereas individual group counseling represents the preferred primary mode of therapy, the use of chemotherapeutic agents has proven to be a useful adjunct in the treatment of anxiety, thereby enabling a seriously afflicted individual to regain productive status while undergoing concurrent psychotherapy.

Compounds of the class of benzodiazepines are currently the therapeutic agents of choice in the treatment of anxiety. In particular, chlordiazepoxide, diazepam and oxazepam are commonly used. This class of compounds has a great potential for misuse, particularly among the class of patients undergoing therapy. Moreover, the benzodiazepines generally possess undesired sedative effects and process detracting interactions with other drugs, including for example, alcohol.

Applicants have now discovered a class of novel aromatic 2-aminoalkyl-1,2-benzoisothiazol-3(2H)one-1,1-dioxide antianxiety agents that are generally free from the undesirable effects of the benzodiazepines. The compounds disclosed herein, when practised in accordance with the teachings of this invention help to alleviate such symptoms as excessive fear, worry, restlessness, tension, stress, neurotic depression and are useful in the relief of some personality disorders. Additionally, the compounds of this invention are effective antihypertensive agents which have the effect of lowering blood pressure in patients in need thereof.

SUMMARY OF THE INVENTION

This invention is directed to a class of aromatic 2-aminoalkyl-1,2-benzoisothiazol-3(2H)one-1,1-dioxide derivatives having the general formula

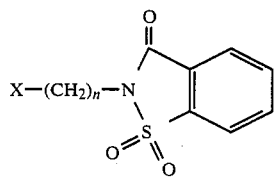

(1)

wherein X is selected from the group consisting of

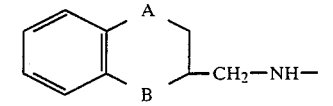

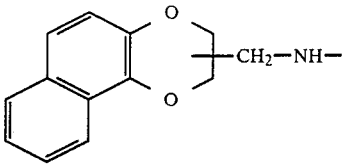

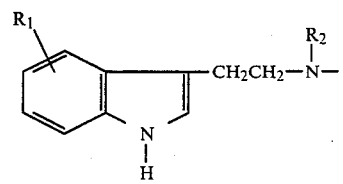

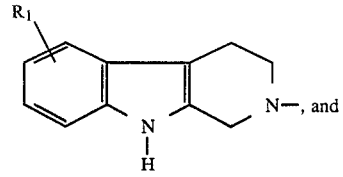

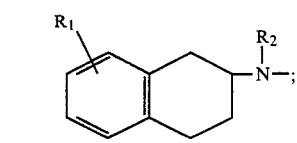

n is an integer of from 2 to 5; A and B are each oxygen, sulfur or NR' where R' represents hydrogen or methyl; $R_1$ is hydrogen, hydroxy or methoxy; $R_2$ is hydrogen or methyl; and the pharmaceutically acceptable acid addition salts thereof.

This invention also discloses a process for the preparation of these compounds and discloses their use as anxiolytic and antihypertensive agents.

DETAILED DESCRIPTION OF THE INVENTION

As used herein the term "pharmaceutically acceptable acid addition salts" is intended to apply to any non-toxic organic or inorganic acid addition salts of the base compounds represented by Formula I. Illustrative inorganic acids which form suitable salts include hydrochloric, hydrobromic, sulphuric and phosphoric acid and acid metal salts such as sodium monohydrogen orthophosphate and potassium hydrogen sulfate. Illustrative organic acids which form suitable salts include the mono, di and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, p-hydroxybenzoic, phenylacetic, cinnamic, salicylic, 2-phenoxybenzoic acids, and sulfonic acids such as methanesulfonic acid or 2-hydroxyethanesulfonic acid. Either the mono or the di-acid salts can be formed, and such salts can exist in either a hydrated or a substantially anhydrous form. In general, the acid addition salts of these compounds are crystalline materials which are soluble in water and in various hydrophilic organic solvents. Additionally, in comparison to their free base forms, such salts generally demonstrate higher melting points and an increased chemical stability.

Specific subclasses of compounds that fall within the scope of the present invention are illustrated as follows:

2-[ω-[(2,3-dihydro-1,4-benzodioxin-2-yl)methylamino]alkyl]-1,2-benzoisothiazol-3(2H)one-1,1-dioxides

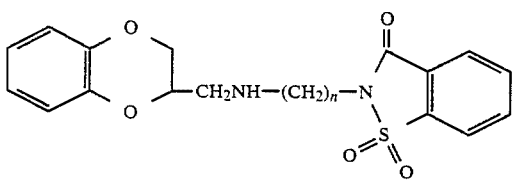
(1a)

2-[ω-[(2,3-dihydro-1,4-benzoxathiin-3-yl)methylamino]alkyl]-1,2-benzoisothiazol-3(2H)one-1,1-dioxides

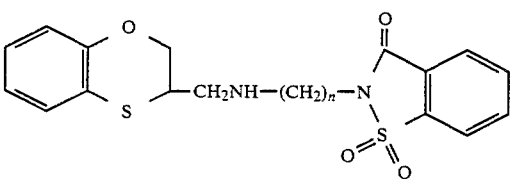
(1b)

2-[ω-[(2,3-dihydro-1,4-benzodithiin-2-yl)methylamino]alkyl]-1,2-benzoisothiazol-3(2H)one-1,1-dioxides

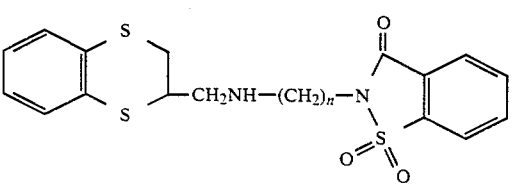
(1c)

2-[ω-[(2,3-dihydro-1,4-benzoxazin-3-yl)methylamino]alkyl]-1,2-benzoisothiazol-3(2H)one-1,1-dioxides

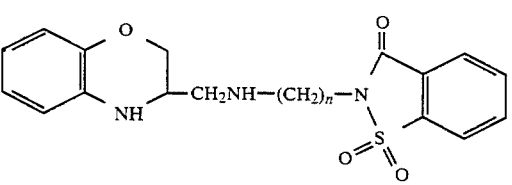
(1d)

2-[ω-[(2,3-dihydroquinazolin-2-yl)methylamino]alkyl]-1,2-benzoisothiazol-3(2H)one-1,1-dioxides

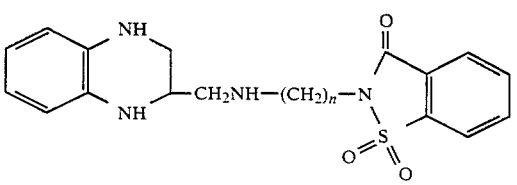
(1e)

2-[ω-[(2,3-dihydronaphtho[1,2-b][1,4]dioxin-2-yl)methylamino]-alkyl]-1,2-benzoisothiazol-3(2H)one-1,1-dioxides

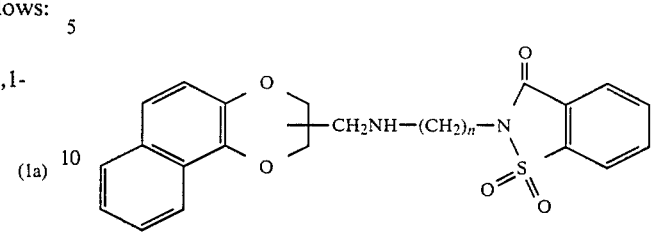

(Compounds of this subclass can be substituted either at the 2- or 3-position of the dioxin ring.)

2-[ω-[substituted (indol-3-yl)ethylamino]alkyl]-1,2-benzoisothiazol-3(2H)one-1,1-dioxides

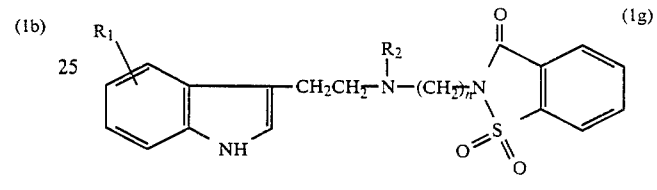
(1g)

2-[ω-[(substituted)1,2,3,4-tetrahydro-β-carbolinyl]alkyl]1,2-benzoisothiazol-3(2H)one-1,1-dioxides

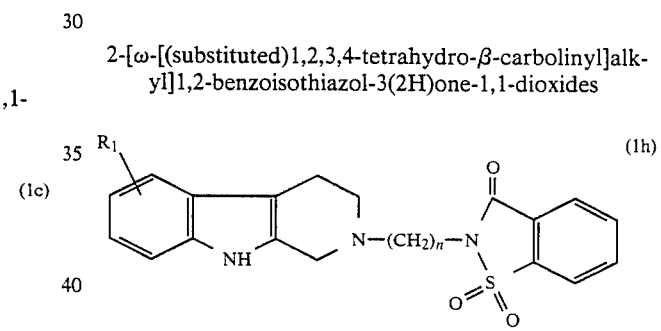
(1h)

2-[ω-[(substituted)-tetralin-2-amino]alkyl]1,2-benzoisothiazol-3(2H)one-1,1-dioxides

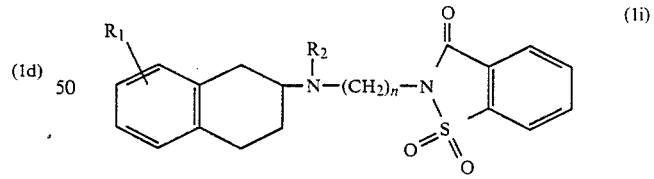
(1i)

A preferred subclass of this invention consists of those compounds of formula (1h) wherein the alkyl chain is terminally substituted with a (substituted)-1,2,3,4-tetrahydro-β-carboline ring system.

A more preferred subclass of this invention relates to those compounds of formula (1f) wherein the alkyl chain is terminally substituted by the 2,3-dihydronaphtho[1,2-b][1,4]dioxin-2-yl or 3-yl ring system.

The most preferred compounds of this invention relate to those compounds of formula (1a) wherein the alkyl chain is terminally substituted by the 2,3-dihydro-1,4-benzodioxin-2-yl ring system.

The alkylene group depicted above —$(CH_2)_n$—, can be considered as a connecting bridge which separates the two terminal heterocyclic ring systems. As indicated, the symbol n can represent an integer of from 2 to 5. Those alkylene groups in which n is from 2 to 4 represent the preferred groups of this invention.

The aromatic 2-aminoalkyl-1,2-benzoisothiazol-3(2H)one-1,1-dioxide derivatives of formula (1) can be prepared in an analogous manner by standard techniques known to those skilled in the art. Thus, the compounds of this invention can be prepared via a condensation of the appropriate nucleophilic amine of formula (2) with an N-alkyl-1,2-benzoisothiazol-3(2H)one-1,1-dioxide substrate of formula (3) as indicated below

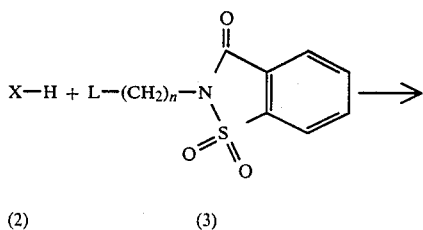

(2)   (3)

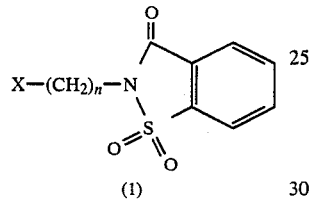

(1)

wherein X and n are as defined in formula (1) and the symbol (L) represents a suitable leaving group, such as chlorine, bromine, iodine, a mesylate or tosylate.

Such a nucleophilic condensation is preferably conducted by reacting approximately equimolar amounts of the nucleophile (2) with the substrate (3), for a period of from about 1 hour to 24 hours depending upon the particular reactants employed. The reaction temperature can range from about 25° C. to 140° C. Preferably the reaction is conducted at a temperature ranging from 60° C. to 125° C.

Additionally, the reaction is preferably conducted in the presence of a tertiary organic base, such as a trialkylamine or pyridine, or in the presence of an inorganic base such as potassium carbonate.

Inasmuch as the reactants employed are typically crystalline materials, the use of solvents is preferred. Suitable solvents include any non-reactive solvent, preferably those having a boiling point in the range of from 60° C. to 150° C. Thus, for example, solvents such as petroleum ethers; chlorinated hydrocarbons such as carbon tetrachloride, ethylene chloride, methylene chloride or chloroform; chlorinated aromatic compounds such as 1,2,4-trichlorobenzene, or o-dichlorobenzene; carbon disulfide; ethereal solvents such as diethylether, tetrahydrofuran or p-dioxane; aromatic solvents, such as benzene, toluene or xylene; or an alcoholic solvent such as ethanol, can be suitably employed. Especially preferred solvents are those which are known to promote nucleophilic reactions, such as dimethysulfoxide and dimethylformamide.

The products of formula (1) can be isolated utilizing appropriate techniques available to those skilled in the art. Thus, for example, the reaction mixture can be filtered to remove solid materials, and the filtrate subsequently evaporated to recover the active ingredient. The compounds of formula (1) can be further purified via recrystallization or by forming and utilizing their picric or oxalic acid complexes.

The nucleophilic primary amines indicated by formula (2) are compounds which are either commercially available or which have been previously described in the literature. Alternatively, the primary amines, designated by the symbol X, wherein $R_2$ is hydrogen, can be readily prepared via a reduction of the corresponding cyano derivatives. Thus, for example, compounds of formula (2), wherein X represents the radical

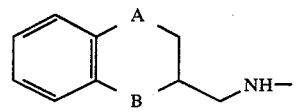

in which A and B are as defined in formula (1) above, are prepared by a reduction of the corresponding cyano derivative (4) shown below

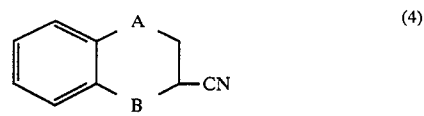   (4)

Such a reduction can be accomplished utilizing a variety of reagent systems, as for example, catalytic reductions employing hydrogen gas with a catalytic metal such as palladium on charcoal, Raney nickel, platinum, rhodium, ruthenium or platinum oxide. In addition, reagents such as diborane, sodium borohydride, dissolving metal reductions utilizing lithium, sodium, potassium, calcium, zinc, magnesium, tin or iron in liquid ammonia or a low-molecular weight aliphatic amine or sodium, aluminum or zinc amalgam, zinc, tin or iron in a hydroxylic solvent or in the presence of an aqueous mineral acid, or lithium aluminum hydride can be favorably employed.

The formula (2) nucleophiles wherein X represents the radical

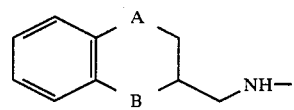

can be prepared by reacting the corresponding cyano compounds with from 1 to 2 molar equivalents of lithium aluminum hydride in an appropriate solvent. Preferably, about 1.5 molar equivalents of hydride are employed. The reaction is allowed to proceed for a period of time ranging from about 30 minutes to about 24 hours. Preferably a time period of from about 1 to 5 hours is employed, depending upon the particular reactants, the solvent and temperature utilized. Suitable temperatures range from −78° C. to 60° C., preferably about 20° C. Suitable solvents include ethereal solvents such as diethyl ether, tetrahydrofuran (THF), p-dioxane, 1,2-dimethoxyethane (DME), diglyme or an aromatic solvent such as benzene, toluene or xylene.

In general, the secondary nucleophilic amines of formula (2), wherein X represents the radicals

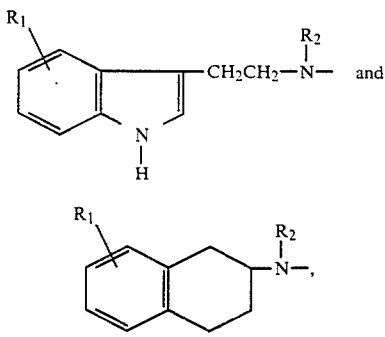

and $R_2$ is other than hydrogen, can be prepared by the direct alkylation of the corresponding primary amine with a suitable alkyl halide, tosylate or mesylate in an appropriate solvent, such as acetonitrile, in the presence of at least one equivalent or an excess of an organic or inorganic base, such as potassium carbonate.

Many of the cyano derivatives of formula (4) are known compounds. Alternatively, these compounds can be prepared in an analogous manner as described below. Thus, for example, utilizing the same example as previously employed the compound

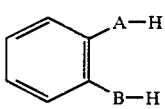

(5)

wherein A and B are as described above, is reacted with 2-bromo or preferably 2-chloroacrylonitrile. Approximately, equimolar amounts of the formula (5) compound and the haloacrylonitrile are mixed with 2 or more molar equivalents of a base, such as potassium carbonate, in an approximate solvent. The reaction is allowed to proceed at a temperature ranging from 0° C. to the boiling point of the reaction mixture, for a period ranging from about 1 to 24 hours. Suitable solvents employed include dimethylformamide; dimethylsulfoxide; acetone; chlorinated hydrocarbons, such as carbon tetrachloride, chloroform or methylene chloride; ethereal solvents, such as diethylether, tetrahydrofuran (THF) or diglyme; aromatic solvents, such as benzene, toluene or xylene; or alcoholic solvents, such as methanol or ethanol.

Where the symbols A and B represent different atoms, a mixture of products will be obtained. These mixtures can be readily separated and purified by methods commonly known to those skilled in the art, such as by chromatography on silica gel or fractional recrystalization. Furthermore, when the $R_1$ or $R_2$ substituents of a compound of formula (1) are hydroxy, the hydroxyl group must be protected prior to undergoing the above described 2-bromo- or 2-chloroacrylonitrile condensation reaction. Suitable protecting groups include the benzyl or methyl groups. These protecting groups are subsquently removed to form the corresponding nucleophilic amines represented by formula (2). The removal of such protecting groups can be by any suitable means generally known to the art, such as the catalytic reduction of the benzyl group, treatment with an acid such as hydrobromic acid, or treatment with boron tribromide.

The compounds of formula (3) are essentially N-alkyl derivatives of saccharin. The leaving groups (L) for compounds of formula (3) can represent any group known to those skilled in the art, such as a tosylate (OTS) or mesylate (OMS), an iodide, bromide or chloride, or hydroxyl group. Formula (3) substrates wherein L is a bromide or an iodide can be prepared by treating the corresponding dihaloalkane with one equivalent of the sodium salt of saccharin in an appropriate solvent for about one hour at a temperature of about 100° C., in accordance with the following reaction scheme.

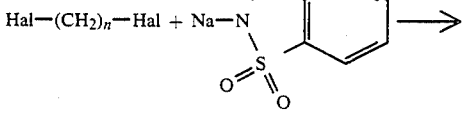

(6)         (7)

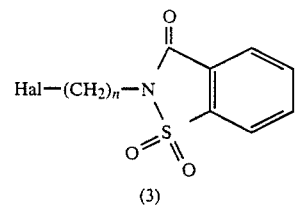

(3)

wherein the symbol Hal represents chloro, bromo or iodo.

Suitable solvents include dimethylformamide; dimethylsulfoxide; acetone; aromatic solvents, such as benzene, toluene or xylene; or an ethereal solvent, such as diethyl ether, tetrahydrofuran (THF) or 1,2-dimethoxyethane (DME).

The compounds of formula (1) possess useful antianxiety and antihypertensive properties. Anxiolytic properties are suggested using $5-HT_{1A}$ in vitro receptor binding studies, see Middlemiss et al., Eur. J. Pharmacol., 90, 151-3 (1983) and Glaser et al., Arch. Pharmacol., 329, 211-215 (1985). The antihypertensive effects of the compounds described herein can be determined both in the anesthetized normotensive rat and/or in the conscious spontaneously hypertensive rat in accordance with the procedure of Fozard, J. Cardiovascular Pharm., 4, 829-838 (1982).

The compounds of this invention can be administered either orally, subcutaneously, intravenously, intramuscularly, intraperitoneally or rectally. The preferred route of administration is oral. The amount of compound to be administered can be any effective amount, and will vary depending upon the patient, the mode of administration and the severity of the anxiety to be treated. Repetitive daily administration of the compounds may be desirable, and will vary depending upon the patient's condition and the mode of administration.

For oral administration, an anxiolytic or antihypertensive effective amount of a formula (1) compound can range from 0.005 to 10 mg/kg of patient body weight per day, preferably from 0.05 to 5 mg/kg of patient body weight per day. The preferred antianxiety dose of the compounds of formula (1a) is about 0.1 mg/kg of patient body weight per day. Pharmaceutical compositions in unit dose form can contain from 1 to 50 mg of active ingredient and can be taken one or more times per day.

For parenteral administration, an anxiolytic or antihypertensive effective amount of a formula (1) compound is from about 0.005 to 10 mg/kg of patient body weight per day, preferably from about 0.05 to 5 mg/kg of patient body weight per day. A parenteral composition in unit dose form can contain from 0.1 mg to 10 mg of active ingredient and can be taken one or more times daily.

For oral administration the compounds can be formulated into solid or liquid preparations such as capsules, pills, tablets, lozenges, melts, powders, solutions, suspensions or emulsions. Solid dosage unit forms generally employed include capsules or tablets. Capsules can be of the ordinary gelatin type which contain additional excipients such as, surfactants, lubricants and inert fillers such as lactose, sucrose and cornstarch. Additionally, the compounds of formula (1) can be tableted with conventional tablet bases such as lactose, sucrose, and cornstarch in combination with binders, such as acacia, cornstarch or gelatin, disintegrating agents such as potato starch or alginic acid, and lubricants such as stearic acid or magnesium stearate.

For parenteral administration the compounds may be administered as injectable dosages of a solution or a suspension of the compound in a physiologically acceptable diluent with or without a pharmaceutical carrier. Suitable diluents or carriers include sterile liquids such as water or oils, with or without the addition of surfactants or other pharmaceutically acceptable adjuvants. Illustrative of various oils that can be employed in the practice of this invention are those of petroleum, animal, vegetable, or synthetic origin, for example, peanut oil, soybean oil, and mineral oil. In general, water, saline, aqueous dextrose and related sugar solutions, ethanol and glycols such as propylene glycol or polyethylene glycol are preferred liquid carriers, particularly for injectable solution.

The following examples illustrate the preparation of representative compounds employed in the practice of this invention, but are not intended to limit the invention in any way thereto.

EXAMPLE I

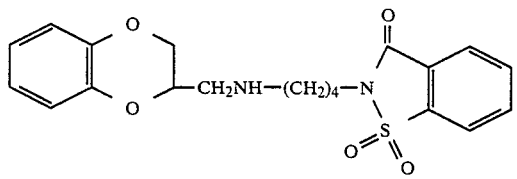

2-[4-[(2,3-Dihydro-1,4-benzodioxin-2-yl)methylamino]-butyl]-1,2-benzoisothiazol-3(2H)one-1,1-dioxide N-(4-Bromobutyl)saccharin Saccharin (9.35 g, 50 mM) in 80 ml of N,N-dimethyl formamide (DMF) is added to 55% sodium hydride (2.18 g, 50 mM) in 20 ml of dry DMF. After 15 minutes, 1,4-dibromobutane (25 ml, 200 mM) is added rapidly, and the mixture is warmed for 1 hour at 100° C. with stirring. The reaction mixture is cooled, filtered and the DMF is evaporated. The crude product is dissolved in methylene chloride and the solution is filtered, dried and evaporated, yielding a yellow oil which is purified by chromatography on silica gel (CH$_2$Cl$_2$/MeOH, 98/2) to afford 13.4 g (84%) of a colorless oil. This oil, when crystallized from isopropanol, yields N-(4-bromobutyl)saccharin having a melting point of 72° C.

NMR CDCl$_3$/TMS 60 MHz 8.20–7.85 (m, 4 H Ar), 4.00–3.30 (m, 4 H), 2.40–180 (M, 4H).

2-[4-[(2,3-Dihydro-1,4-benzodioxin-2-yl)methylamino]-butyl]-1,2-benzoisothiazol-3(2H)one-1,1-dioxide hydrochloride 2-Aminomethyl-benzodioxan[1,4] (0.965 g, 5.48 mM), potassium carbonate (3 g) and N-(4-bromobutyl)-saccharin (1.43 g, 4.5 mM), prepared as above, are mixed in N,N-dimethylformamide (DMF, 10 ml). The mixture is stirred at 100° C. overnight, cooled, filtered and evaporated to dryness. The residue is dissolved in ethyl acetate, washed with water and acidified with dilute hydrochloric acid. The oil which separates is washed with ether, 5% HCl, water, dissolved in methanol, dried and evaporated to dryness, affording 1.3 g of a crude yellow solid. This material is converted to the free base and flash-chromatographed on silica (CH$_2$CO$_2$/'MeOH 97/3), yielding 0.91 g of the desired compound. The hydrochloride salt is recrystallized from an isopropanol/ethyl acetate solution to yield the title compound having a melting point of 210° C.

Following essentially the same procedure but substituting N-(2-bromoethyl)saccharin for the N-(4-bromobutyl)saccharin above, the compound 2-[2-[(2,3-dihydro-1,4-benzodioxin-2-yl)methylamino]ethyl]-1,2-benzoisothiazol-3(2H)one-1,1-dioxide is obtained, having a melting point of 181° C.

EXAMPLE II

2-[4-(2-[1,2,3,4]-tetrahydro-β-carbolinyl)butyl]-1,2-benzoisothiazol-3(2H)one-1,1-dioxide Following essentially the same procedure as in Example I, but substituting [1,2,3,4]-tetrahydro-β-carboline for 2-aminomethyl-benzodioxan[1,4], the title compound was prepared and crystallized as a hydrochloride, having a melting point of 272° C.

EXAMPLE III

2-[4-[8-Methoxytetralin-2-amino]butyl]1,2-benzoisothiazol3(2H)one-1,1-dioxide

Following essentially the same procedure as in Example I, but substituting 8-methoxy-2-aminotetralin for 2-aminomethylbenzodioxan[1,4], the title compound was prepared and crystallized as a hydrochloride, having a melting point of 233° C.

EXAMPLE IV

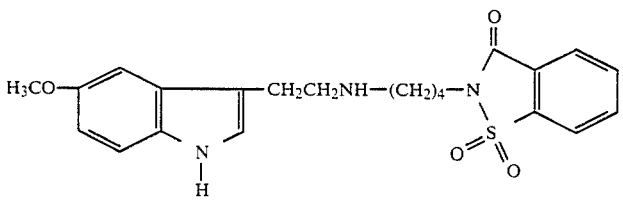

2-[4-[5-Methoxy-indol-3-yl)ethylamino]butyl]1,2-benzoisothiazol-3(2H)one-1,1-dioxide Following essentially the same procedure as in Example I, but substituting 5-methoxy-tryptamine for 2-aminomethyl-benzodioxan[1,4], the title compound was prepared and crystallized as a hydrochloride, which decomposes prior to melting.

1H NMR (free base, $CDCl_3+CD_3OD$, 360 MHz, ppm): 8.4 (1H,s), 8.0–7.7 (4H,m), 7.2–6.75 (4H,m), 3.8 (3H,s), 3.8–3.6 (2H,m), 3.15 (4H,m), 2.9 (2H,t), 1.85 (4H,m).

EXAMPLE V

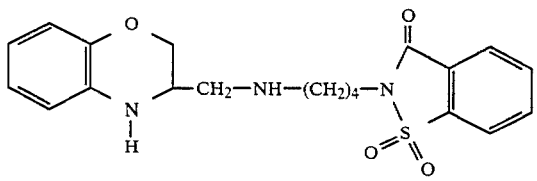

2-[4-[(2,3-Dihydro-1,4-benzoxazin-3-yl)methylamino]butyl]-1,2-benzoisothiazol-3-(2H)one-1,1-dioxide Following essentially the same procedure as in Example I, but substituting 2-aminomethylbenzoxazin for 2-aminomethylbenzodioxan[1,4], the title compound was prepared and crystallized as a hydrochloride, having a melting point of 209° C.

EXAMPLE VI

In vitro Determination of Anxiolytic Properties via $5\text{-}HT_{1A}$ Binding

Radioligand binding studies of the $5\text{-}HT_{1A}$ recognition sites were carried out as follows: male normotensive Sprague-Dawley rat frontal cortex was dissected, frozen in liquid nitrogen and stored at −20° C. until needed. Tissues from 4–8 rats were pooled and homogenised in 70 vol Tris-HCl buffer (50 mM, pH 7.7), using a kinematica Polytron (setting 2/3 max speed, 20 sec). The homogenate was centrifuged (36500×g for 10 min), the pellet re-homogenised in the same volume of buffer and the process repeated two more times. Between the second and third centrifugations the tissue homogenate was incubated at 37° C. for 10 min. The final pellet was suspended in the same volume of Tris buffer containing 10M pargyline, 5.7 mM $CaCl_2$ and 0.1% ascorbic acid. This suspension was incubated for 10 min at 37° C. and then stored on ice until used in the binding assay.

Tissue homogenate (0.7 ml), radioactive ligand (0.1 ml) and the appropriate concentration of test compound (0.1 ml), together with buffer to a final volume of 1 ml were incubated at 37° C. for 15 min. Incubations were terminated by rapid filtration through Whatman GF/B filters followed by three 5 ml washes with ice-cold Tris-HCl buffer (50 mM, pH 7.0). Radioactivity was measured after extraction into Aquasol-Z (NEN) at an efficiency of 45–50%. The radioligand used to label the $5\text{-}HT_{1A}$ recognition sites and its concentration is [$^3$H]-8-hydroxy-2-(di-n-propylamino)-tetralin, ([$^3$H]-8-OH-DPAT), 1 mM.

Following essentially the above procedure, the following compounds were tested. Results are expressed as $pIC_{50}$ ($\log_{10}$ concentration of test compound which inhibits specific binding by 50%), and represent the means ±S.E.M. of 3 independent experiments.

| Test Compound | $5\text{-}HT_{1A}$ Binding Affinity Rat Brain Cortex | *Fold Increase |
| --- | --- | --- |
| Buspirone | 7.52 ± 0.10 | 1 |
| Example I(A) | 9.34 ± 0.03 | 66 |
| Example II | 8.16 ± 0.07 | 4.4 |
| Example III | 8.52 ± 0.14 | 10 |
| Example V | 8.03 ± 0.15 | 3.2 |

*Antilog of the difference of the test compound compared to buspirone

As indicated in the above data, the compounds tested represent a 3 to 60 fold increase in potency, based upon $5HT_{1A}$ binding studies, when compared to buspirone.

EXAMPLE VII

Determination of Antihypertensive properties

Male, normotensive Sprague-Dawley rats weighing 250–350 g (supplied by Charles River, France) were anesthetized with pentobarbitone sodium, 60 mg/kg, i.p., plus 15 mg/kg s.c. Blood pressure was recorded either from the left common carotid artery or from a femoral artery by means of a Statham pressure transducer (Type P23 AA) and heart rate was recorded from the electrocardiogram using a Beckman cardiotachometer coupler (Type 9757 B). Records were displayed on a Beckman dynograph (Type R). A femoral vein was cannulated for the intravenous injection of drugs. After completion of all operative procedures, heparin 500 U was injected intravenously.

The compounds of Example I, 2-[4-[(2,3-dihydro-1,4-benzodioxine-2-yl)methylamino]butyl]-1,2-benzoisothiazol-3(2H)one-1,1-dioxide was administered s.c. as a saline solution in a volume of 1 ml/kg body weight. The following changes in blood pressure (B.P.) and heart rate (H.R.) were observed.

| Dose | Δ BP (mmHg) | Δ HR (beats/min) |
| --- | --- | --- |
| 25 μg/kg | −35 | −80 |
| 500 μg/kg | −50 | −90 |

In a separate experiment arterial blood pressure and heart rate were measured directly in conscious male, spontaneously hypertensive rats weighing 250–350 g (Charles River, France). The same test compound was administered, either s.c. or orally, as a saline solution of 1 ml/kg body weight in the doses shown below.

| Route and Dose | Δ BP (mmHg) | Δ HR (beats/min) |
| --- | --- | --- |
| 100 μg/kg s.c. | −20 | +80 |
| 200 μg/kg s.c. | −65 | +100 |
| 500 μg/kg s.c. | −75 | +120 |
| 1 mg/kg per os. | −25 | +100 |
| 5 mg/kg per os. | −45 | +100 |

In short, under the conditions tested, it can be said that the compound, 2-[4-[(2,3-dihydro-1,4-benzodioxin-2-yl)methylamino]butyl]1,2-benzoisothiazol-3(2H)one-1,1-dioxide effectively lowers the blood pressure and heart rate in anesthetized normotensive rats, and lowers the blood pressure with reflex tachycardia in conscious spontaneously hypertensive rats.

We claim:

1. An aromatic 2-aminoalkyl-1,2-benzoisothiozol-3(2H)one-1,1-dioxide derivative having the formula

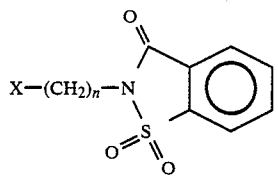

wherein n is an integer of from 2 to 5;
X is

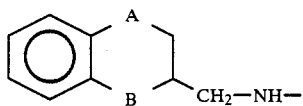

wherein one of A and B is a sulfur and the other is =NR′ wherein R′ is hydrogen or methyl; or a pharmaceutically acceptable acid addition salt thereof.

2. An aromatic 2-aminoalkyl-1,2-benzoisothiazol-3(2H)one-1,1-dioxide derivative of claim 1 wherein n is an integer of from 2 to 4.

3. An aromatic 2-aminoalkyl-1,2-benzoisothiazol-3(2H)one-1,1-dioxide derivative of claim 1 wherein n is the integer 4.

4. An aromatic 2-aminoalkyl-1,2-benzoisothiazol-3(2H)one-1,1-dioxide derivative of claim 1 wherein A is a sulfur and B is an NR′.

5. An aromatic 2-aminoalkyl-1,2-benzoisothiazol-3(2H)one-1,1-dioxide derivative of claim 4 wherein n is an integer of from 2 to 4.

6. An aromatic 2-aminoalkyl-1,2-benzoisothiazol-3(2H)one-1,1-dioxide derivative of claim 4 wherein n is the integer 4.

7. An aromatic 2-aminoalkyl-1,2-benzoisothiazol-3(2H)one-1,1-dioxide derivative of claim 1 wherein A is a sulfur and B is an NR′ wherein R′ is hydrogen.

8. An aromatic 2-aminoalkyl-1,2-benzoisothiazol-3(2H)one-1,1-dioxide derivative of claim 7 wherein n is an integer of from 2 to 4.

9. An aromatic 2-aminoalkyl-1,2-benzoisothiazol-3(2H)one-1,1-dioxide derivative of claim 7 wherein n is the integer 4.

10. A method for relieving the symptoms of anxiety in a patient in need thereof, which comprises the administration to said patient of an anxiolytic effective amount of a compound of one of claims 1–9.

11. A method for lowering blood pressure in a person in need thereof, which comprises the administration to said patient of an antihypertensive effective amount of a compound of one of claims 1–9.

12. An anxiolytic composition comprising an anxiolytic effective amount of a compound according to one of claims 1–9, or a pharmaceutically acceptable acid addition salt thereof, in combination with a pharmaceutically acceptable carrier or diluent.

13. An antihypertensive composition comprising an antihypertensive effective amount of a compound according to one of claims 1–9, or a pharmaceutically acceptable acid addition salt thereof, in combination with a pharmaceutically acceptable carrier or diluent.

* * * * *